US006363800B1

(12) United States Patent
Call et al.

(10) Patent No.: US 6,363,800 B1
(45) Date of Patent: Apr. 2, 2002

(54) COATING TO ENHANCE THE EFFICIENCY OF A PARTICLE IMPACT COLLECTOR

(75) Inventors: Charles Call, Pasco; James Millar, West Richland, both of WA (US)

(73) Assignee: MesoSystems Technology, Inc., Kennewick, WA (US)

(*) Notice: Subject to any disclaimer, the term of this patent is extended or adjusted under 35 U.S.C. 154(b) by 0 days.

(21) Appl. No.: 09/265,620

(22) Filed: Mar. 10, 1999

(51) Int. Cl.[7] .............................................. G01N 15/02
(52) U.S. Cl. .................................................. 73/863.22
(58) Field of Search ............................ 73/28.05, 28.06, 73/863.21, 863.22; 435/309.1; 96/413

(56) References Cited

U.S. PATENT DOCUMENTS 3,760,630 A * 9/1973 Brumbaugh ............... 73/28.05
3,970,428 A * 7/1976 Barringer ................. 73/863.22
4,255,172 A * 3/1981 Smith ...................... 73/863.22
4,590,792 A * 5/1986 Chiang ...................... 73/28.06
4,947,839 A * 8/1990 Clark et al.
4,961,966 A * 10/1990 Stevens et al.
5,304,125 A * 4/1994 Barringer ................. 73/863.22

* cited by examiner

*Primary Examiner*—Robert Raevis
(74) *Attorney, Agent, or Firm*—Roland M. Anderson

(57) ABSTRACT

Apparatus and a method for separating particulates from a fluid in which the particulates are entrained. An impact collection surface is coated with a material that improves the efficiency with which the particulates are separated from the fluid and collected. In one embodiment, the coating retains the particulates when dry, but readily releases the particulates when wetted with a liquid. In another embodiment, the coating is a material that has a relatively low coefficient of friction, so that the particulates that have impacted on the coating are readily washed from it with a liquid. The coating may be selected to retain specific biological particulates by including an antibody that selectively links with antigens on the biological particulates. The coated impact collection surface may be used to purify water by removing biological contaminants and other particulates from the water passing over the coated impact collection surface. In one embodiment of a particle impact collector using coatings like those just described, the coated impact collection surface is on a flexible tape that is moved past a point of collection and onto a take-up reel.

40 Claims, 3 Drawing Sheets

COATING TO ENHANCE THE EFFICIENCY OF A PARTICLE IMPACT COLLECTOR

FIELD OF THE INVENTION

This invention generally relates to particle impact collectors, and more specifically, to a coating for a surface used in connection with a particle or aerosol impact collector.

BACKGROUND OF THE INVENTION

It is often necessary to separate particulates from air or other fluids in which the particulates are entrained. For example, aerosols comprising small droplets of liquid dispersed into air are not easily analyzed unless the aerosol materials are separated from the air to produce a more concentrated sample that can then be analyzed. The aerosols or particulates can be liquids, solids, or semi-solids that are sufficiently small to be dispersed within and carried about in air and may include inorganic or organic chemicals, or living materials, e.g., bacterial cells or spores. Also, solids or semi-solids can be introduced into a liquid that is then dispersed within air as an aerosol mist so that the solids are carried within the liquid droplets comprising the aerosol mist.

Generally, it is difficult to identify materials comprising particulates entrained in a gaseous fluid unless the particulates can be collected by separating them from the air or other gaseous fluid and concentrated in a specimen suitable for analysis. In addition to identifying the type of particulates entrained in a gaseous fluid, it may be important to classify the size of the particulates. For example, when checking stack emissions, it is usually important to determine the materials carried as particulates within the emissions and the size of the particulates to determine whether the emissions conform to pollution control limits.

Particle impact devices are commonly used for collecting particulates from gaseous streams in which they are dispersed. Conventional particle impactor collectors employ circuitous paths with many abrupt changes of direction along the passages through which a particulate laden fluid flows. The particulates, being substantially more massive than the molecules of the fluid in which they are entrained, fail to negotiate the abrupt turns in these passages and are thus separated from the moving fluid stream, collecting on the surfaces that they impact. To function properly, such prior art particle impactors require that the gaseous fluid stream be moved through the impactor at least at some minimum velocity. A fan is typically used to provide the required velocity to the fluid flowing into the particle impact collector. One problem with particle impact collectors of this type is that it is often difficult to separate the particulates collected from the surfaces on which they have impacted. Furthermore, many of the particulates do not collect on the desired collection surfaces and are therefore unavailable for analysis and evaluation.

Another type of prior art particle impact collector includes a rotating arm that is placed within the flow path of a fluid in which particulates are entrained. The particulates impacting the rotating arms are separated from the fluid and subsequently stripped from the surfaces of the arms. However, such collectors do not provide a simple and efficient mechanism to remove the particulates from the rotating arms.

Virtual impactors are another type of prior art device used for separating particulates from a gaseous fluid, again using the differences in mass of the particulates and the fluid molecules to facilitate the separation process. In this type of device, the gaseous fluid is directed along a passage and separated by a divider disposed within the passage into a fast moving major stream and a much slower moving minor stream. The more massive particulates remain in the slower moving minor stream, while the fluid and very small particulates continue through the device in the major stream. However, virtual impactors simply separate the streams, but do not provide a specific collection mechanism for separating the particulates from the fluid in which they are carried.

Although other types of particle impact collectors and virtual impactors are described in the prior art, none of them employ a coating element on the impactor surface to enhance the efficiency with which particulates entrained in a gaseous fluid are collected. Further, none of these prior art devices provide an efficient mechanism for releasing the particulates collected on the impactor surfaces so that the particles may be analyzed. Clearly, it would be desirable to increase the collection efficiency of a particulate impactor, both in regard to the separation of particulates from the gaseous fluid in which they are entrained, and in connection with removal of the particulates from the surfaces of the device on which they have collected.

SUMMARY OF THE INVENTION

The present invention relates to a method for separating particulates from a fluid in which the particulates are entrained. The method includes the steps of providing an impact collection surface and applying a coating of a material to the surface. This material increases the retention of the particulates impacting the material coating the impact collection surface when the material is dry, but readily releases the particulates that have been collected thereon when the material is wetted. The fluid in which the particulates are entrained is caused to flow toward the coated impact collection surface, so that the particulates are retained by the material and are thus separated from the fluid.

In one embodiment, the impact collection surface comprises a surface of a tape. The coating is applied to selected portions of the surface of the tape to produce the coated impact collection surface. The method further includes the step of advancing the tape, so that new areas that are coated with the material are impacted by the particulates entrained in the fluid. In another form of the invention, the impact collection surface includes projecting structure that enhances the collection of particulates. For example, the projecting structure may comprise a plurality of ridges or rods that are relatively small and extend outwardly.

In one form of the invention, the material comprising the coating has the property of attracting only particulates of a specific desired type. For example, the desired type of particulates can be biological in nature. In this case, the coating comprises an antibody selected so that only particulates having a corresponding antigen are retained by the coating. It is thus contemplated that the particulates retained by the coating may comprise a disease causing organism.

In another embodiment, the material comprising the coating is characterized by having a first state and a second state. When the material is in its first state, it attracts the particulates, but when it is in the second state, it releases the particulates. The method thus further comprises the step of causing the material to be in the first state to separate the particulates from the fluid. After a defined period of time has elapsed during which the particulates are separated from the fluid and retained by the coating, the method also includes the step of causing the material comprising the coating to change from its first state to its second state. The particulates that have been separated from the fluid and then released from the material when the material changes to its second state and collected. The step of collecting preferably includes the steps of directing a liquid toward the coated impact collection surface, so that the particulates separated from the fluid are carried away from the surface by the liquid, and collecting the liquid carrying the particulates. In one form of the invention, the step of causing the material to change from the first state to the second state comprises the step of wetting the material with the liquid. In this form of the invention, the material preferably comprises TETRAGLYME, and the liquid preferably comprises water. TETRAGLYME is a common chemical name for bis(2-[methoxyethoxy]ethyl) ether tetraethylene glycol dimethyl ether dimethoxy tetraethylene glycol.

Another type of material used for the coating is characterized by having a relatively low coefficient of friction, so that the particulates initially retained thereon by impacting the coating readily detach from the coating.

The method may also include the step of directing a liquid towards the coating to wash away the particulates that have been separated from the fluid. The liquid and the particulates washed away from the coated impact collection surface are then collected. The liquid preferably comprises water.

Another aspect of the present invention is directed to a method for removing pathogens from a fluid. This method includes the step of providing a particle impact collector having a surface coated with a material that is in either a first or a second state. The first state of the material is characterized by its ability to retain the pathogens and thereby separate them from the fluid. The second state of the material is characterized by its ability to readily release the pathogens. The method includes the step of causing the material to be maintained in the first state. The fluid in which the pathogens are entrained is directed toward the surface, so that the pathogens are retained by the material coating the surface while it is in the first state. These pathogens are thereby removed from the fluid to purify it. After an interval of time in the first state, the state of the material coating the surface is changed to the second state. The pathogens retained by the coating are then released, thereby cleansing the surface so that it may be reused to again purify the fluid.

Yet another aspect of the present invention is directed to apparatus for separating particulates from a fluid in which they are entrained. The various embodiments of the apparatus include elements that are generally consistent with the steps of the method discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
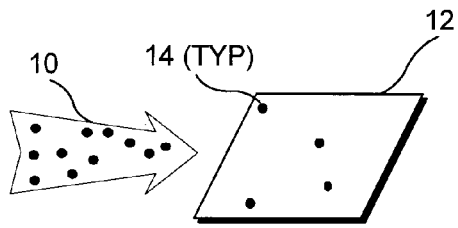
FIG. 1 (prior art) is a schematic view of a fluid in which particulates are entrained, impacting an uncoated impact collection surface.
Figure 2:
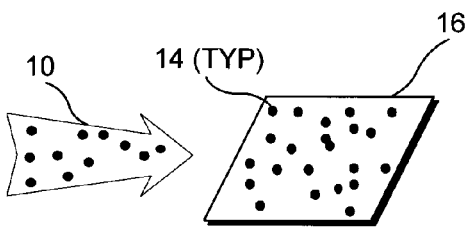
FIG. 2 is a schematic view of a fluid in which particulates are entrained, impacting a coated impact collection surface in accord with the present invention.

FIGS. 1 and 2 schematically illustrate how coating an impact collection surface with a material in accord with the present invention can substantially enhance the efficiency of that surface. FIG. 1 shows a fluid 10 in which particulates 14 are entrained, moving relative to a (prior art) impact collection surface 12 that is not coated. Particulates 14 are separated from the fluid by striking against impact collection surface 12. FIG. 2 shows fluid 10 moving toward a coated impact collection surface 16, which has been coated with a material that retains substantially more of the particulates entrained in fluid 10. By comparison of these FIGS. 1 and 2 it will be apparent that significantly more particulates 14 are collected on coated impact collection surface 16 than on impact collection surface 12.

As used in this description and in connection with the present invention as defined by the claims that follow, the term "particulates" is intended to encompass aerosols, liquids, solids, or semi-solids that are sufficiently small to be dispersed within and carried about in a gaseous fluid and may include inorganic or organic chemicals, or living materials, e.g., bacterial cells or spores. Also included in this term are solids or semi-solids that have been introduced into a liquid, which is then dispersed within a gaseous fluid such as air as an aerosol mist, so that the solids or semi-solids are carried within the liquid droplets.

The relatively greater density of particulates 14 evident on coated impact collection surface 16 compared to impact collection surface 12 is due to a characteristic of the coating to better retain particulates and thus more efficiently separate the particulates from the fluid in which they are entrained, compared to the prior art impact collection surface that is not coated. In this first embodiment of the present invention shown in FIG. 2, the geometry of impact collection surface 16 is generally irrelevant. The coating of the present invention can be applied to the impact collection surfaces in virtually any impact collector. Simply by coating the impact collection surfaces of an impact collector with one of the materials described below, a substantial increase in the efficiency with which particulates are separated from a fluid and collected is achieved.

Figure 3:
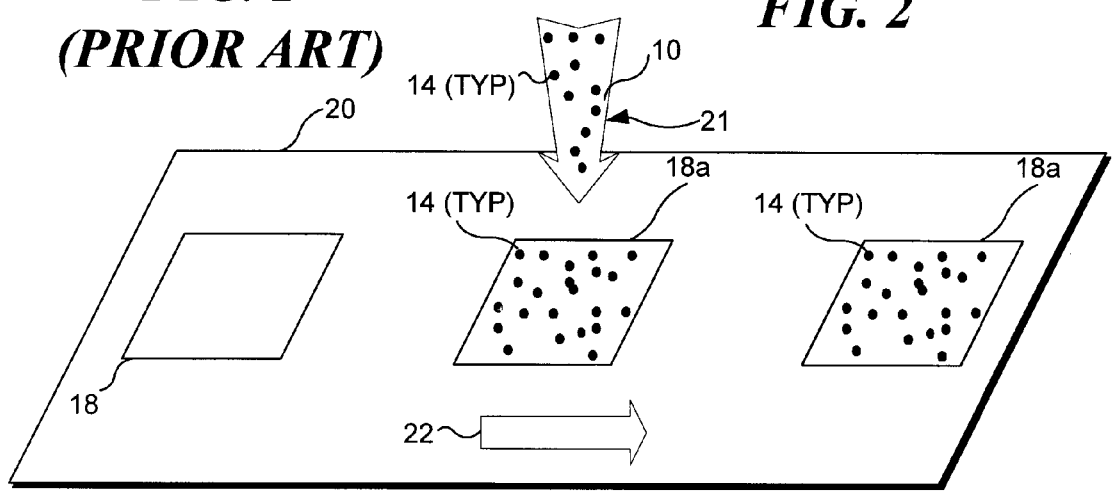
FIG. 3 is a schematic view of a flexible tape having a coated impact collection surface.

FIG. 3 schematically illustrates an embodiment of the present invention in which a plurality of coated areas 18 are applied to an upper exposed surface of an elongate tape 20. As illustrated in this Figure, tape 20 is advanced from left to right, i.e., in the direction indicated by an arrow 22. Tape 20 thus moves past a stream 21 of fluid 10 in which particulates 14 are entrained. Stream 21 is directed toward the upper surface of the tape. As the tape advances, fresh coated areas 18 are exposed to impact by particulates 14. The particulates that impact on these coated areas are at least initially retained thereon, as shown in coated areas 18a. In the embodiment illustrated in FIG. 3, coated areas 18 and 18a are not contiguous; but instead are discrete patches disposed in spaced-apart array along the longitudinal axis of tape 20. Various types of material described below can be used to produced coated areas 18.

Figure 4:
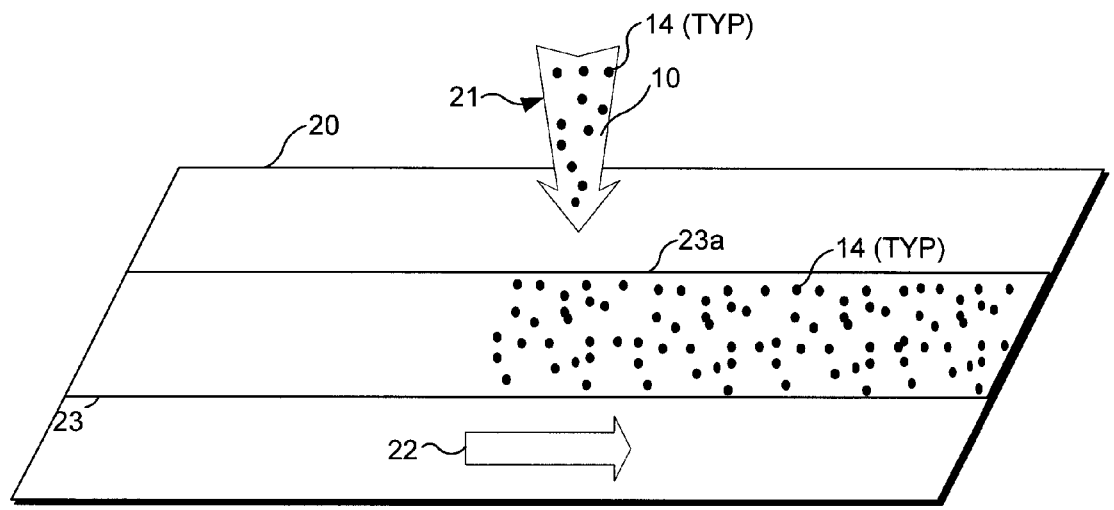
FIG. 4 is a schematic view of a flexible tape having a coated impact collection surface which is advanced past a collection point by a rotating take-up reel.

In an alternative embodiment shown in FIG. 4, a continuous coated impact collection surface 23 extends longitudinally along the center of a tape 20'. As tape 20' advances in the direction indicated by arrow 22, stream 21 of fluid 10 with entrained particulates 14 is directed toward the upper surface of the tape. Particulates 14 are retained by the coating, as shown in a coated impact collection surface 23*a*. As tape 20' advances in direction 22, coated impact collection surface 23 is exposed to impact by particulates 14 carried in stream 21. In the embodiment that is illustrated, the coating does not cover the entire upper surface of tape 20'. However, it should be understood that any portion or the entire upper surface of tape 20' can be covered with the coating. The various types of material contemplated for the coating are discussed below.

Figure 5:
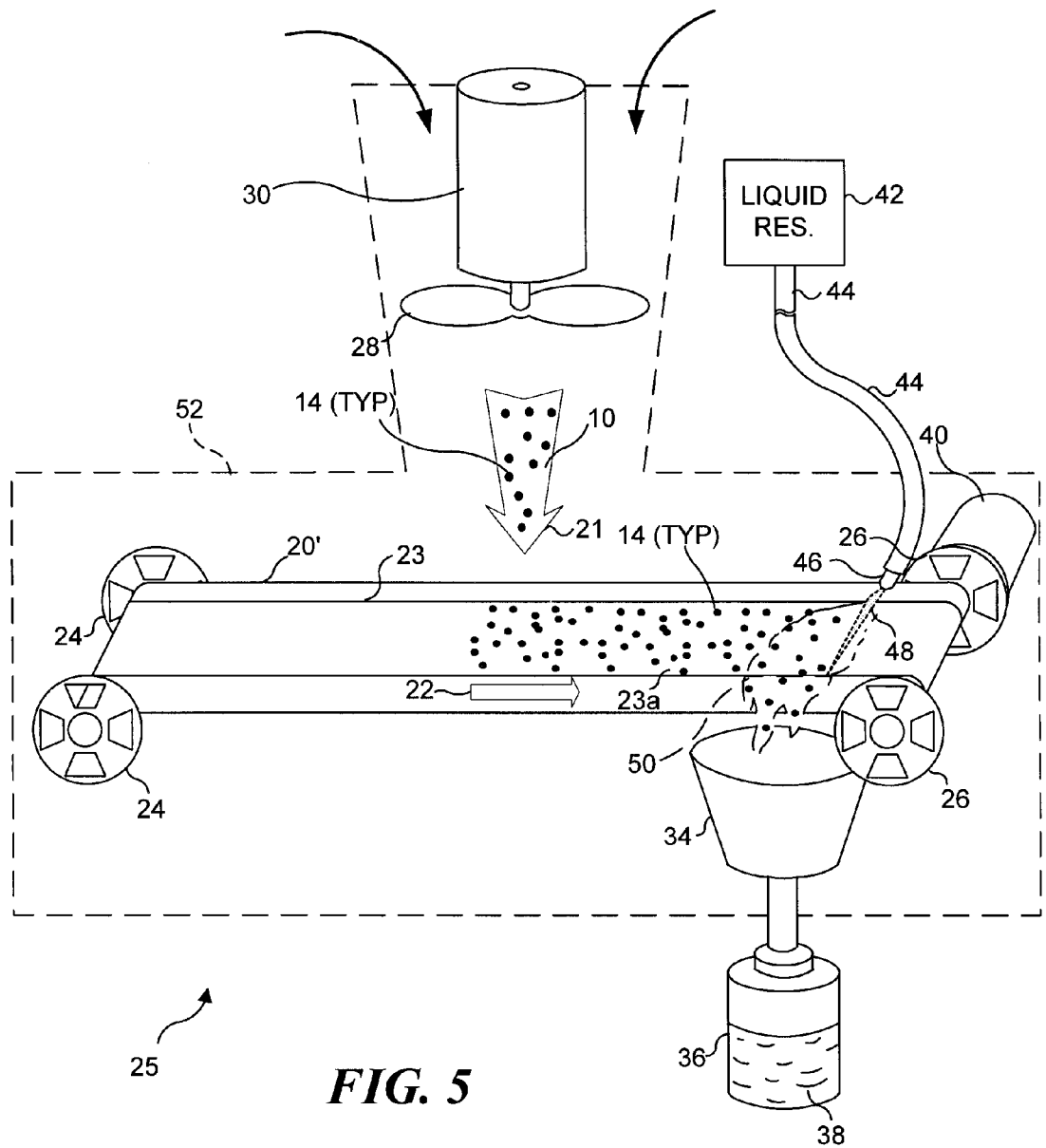
FIG. 5 is a schematic view of a particle impact collector using a flexible tape having a coated impact collection surface.

FIG. 5 schematically illustrates a particle impact collector 25 that includes tape 20' with coated impact collection surface 23. Other elements of the collector include a fan 28, which is rotatably driven by an electric motor 30. Fan 28 impels fluid 10 in stream 21 toward coated impact collection surface 23. Other types of fans or impellers can alternatively be used. For example, a centrifugal fan (not shown) can be employed to move the fluid. If the fluid in which the particulates are entrained is a liquid, a pump (not shown) would be used instead of fan 28 to move fluid 10 toward coated impact collection surface 23. The tape 20' advances from a supply reel 24 onto a take-up reel 26. An electric motor 40 coupled to take-up reel 26 rotates the take-up reel at a selected speed so that the tape passes under stream 21 of fluid 10. Particulates 14 impact on the coated impact collection surface of the tape and are carried toward the take-up reel by the moving tape.

To collect a concentrated sample of particulates 14 from those retained on coated impact collection surface 23*a*, particle impact collector 25 may include a specimen container 36 that is coupled with a funnel 34. A liquid 38 that is rich in the particulates previously retained on the coated impact collection surface partially fills specimen container 36. Liquid 38 is obtained by washing the particulates from the tape. A reservoir 42 is included to supply the liquid for this purpose. The liquid from the reservoir is conveyed through a fluid line 44 and sprayed toward tape 20' through a nozzle 46, which creates a fan-shaped spray 48. If necessary, a pump, e.g., a centrifugal or a peristaltic pump (not shown) may be used to force the liquid through nozzle 46 under sufficient pressure to wash away the particulates retained by the coated impact collection surface. These particulates are carried by a stream 50 of the liquid into funnel 34 and thus, into specimen container 36.

The material used for producing coated impact collection surface 23 and other coated areas or surfaces employed in this description for collecting particulates in accord with the present invention is selected because of certain characteristics of the material that increase the efficiency with which the particulates are separated from the fluid in which they are entrained. Each material used for a coating has certain advantages that may make it preferable compared to other materials for separating a specific type of particulate from a specific type of fluid. For example, for use in particle impact collector 25, a material called TETRAGLYME can be used to for the coating. This material is hydrophilic until it is exposed to water and when dry, is relatively very sticky, tending to readily retain particulates that impact it. However, once water is sprayed onto the TETRAGLYME coated surface so that it is wetted, the coating becomes hydrophobic. When hydrophobic, the TETRAGLYME coated surface is no longer sticky or tacky, and in fact, readily releases the particulates that previously were retained by it. The water (or other liquid containing water) easily washes the particulates away from the coated impact collection surface, as described above. TETRAGLYME, which is available from chemical supply houses, is bis(2-ethyl) ether tetraethylene glycol dimethyl ether dimethoxy tetraethylene glycol and has the formula: $CH_3OCH_2$ $(CH_2OCH_2)_3$ $CH_2OCH_3$ $CH_3$—O—$CH_2$—$CH_2$—O—$CH_2$—$CH_2$—O—$CH_2$—$CH_2$—O—$CH_2$—$CH_2$—O—$CH_3$. Test have shown that TETRAGLYME coating can collect more than three times as many particulates as an uncoated surface. Water molecules are retained by the molecule by links to the oxygen atoms, as shown below.

$$O{:}H_2O{:}O$$

A second type of material usable for the coated impact collection surface is PARYLENE, which is a tetrafluoromore manufactured and sold by Dupont Chemical Company under the trademark INSUL-COTE™, Type N. The PARYLENE material is characterized by a relatively low coefficient of friction, causing it to be extremely slippery and not sticky. Accordingly, particulates impacting against a coated surface comprising PARYLENE are initially separated from the fluid in which they are carried by the impact with the coated surface and are initially retained by the coated surface. However, these particulates are readily washed away from the PARYLENE coated surface by water or other liquid sprayed onto the coating. It will be apparent that PARYLENE is also usable as a coating for the coated impact collection surface in particle impact collector 25. The particulates retained by a PARYLENE coated surface on tape 20' are readily washed away from the coating by water or other liquid comprising spray 48.

The TETRAGLYME material is an example of a class of materials that have two distinct states related to particulate collection. When dry and hydrophilic, the TETRAGLYME material is in a first state, in which it is sticky and is very efficient at separating particulates from the fluid in which they are entrained, compared to an uncoated surface. However, when wetted, the TETRAGLYME material changes to its second state, in which it readily releases the particulates.

Figure 6:
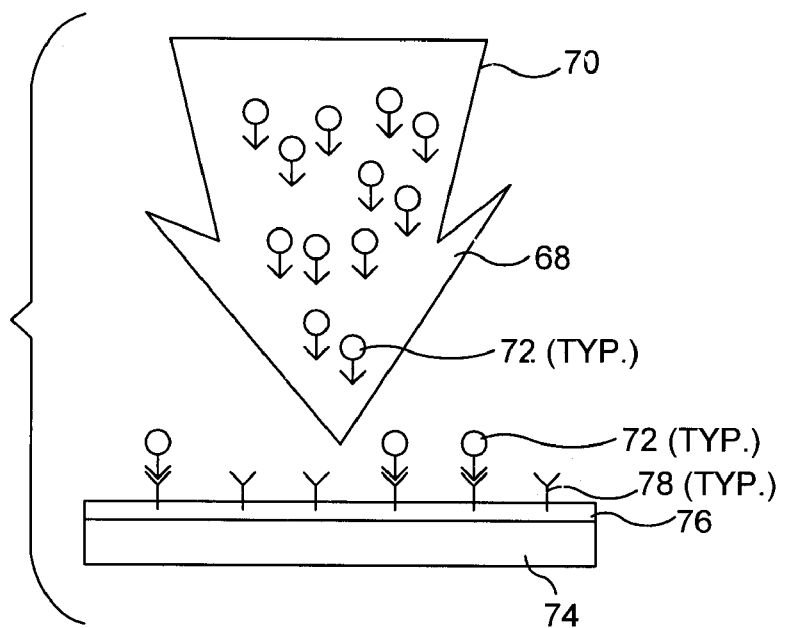
FIG. 6 is a schematic illustration illustrating an impact collection surface coated with a material that includes antibodies that link with an antigen on a specific biological particulate.

As shown in FIG. 6, a mono-layer material 76 can be applied to a surface 74 of a particle impact collector of other device, to separate specific biological particulates 72 from a fluid 68 such as air or a liquid in which they are entrained. It is contemplated that the fluid conveying the biological particulates may also include blood. A stream 70 of the biological particulates is directed at material 76, so that the biological particulates impact thereon. Mono-layer material 76 comprises a plurality of antibodies 78 that are selected to link with the antigens on biological particulates 72. Thus, for example, if biological particulates 72 comprise anthrax spores, and antibodies 78 are selected that are specific to anthrax spores, the anthrax spores will be readily separated and retained by linking with the antibodies on the coating. These anthrax spores may then be identified based upon analyses that are outside the scope of this disclosure.

Figure 7A:
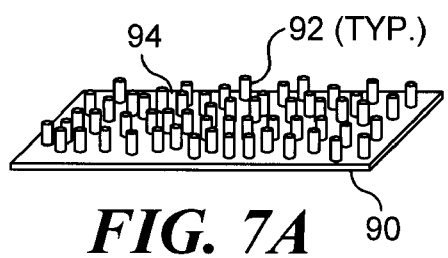
FIGS. 7A and 7B illustrate two embodiments in which outwardly projecting structures are provided on an impact collection surface to enhance particulate collection.
Figure 7B:
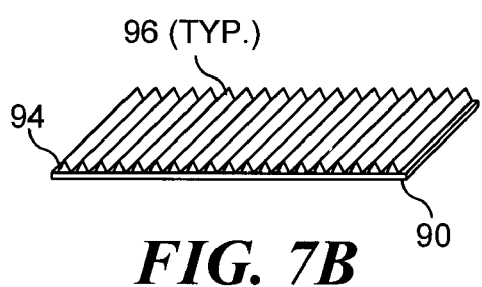

It is also contemplated that the coated impact collection surface need not be planar. Indeed, it is likely that an enhanced particulate collection efficiency can be achieved by using a non-planar coated surface to collect particulates. FIG. 7A illustrates an enlarged view of a portion of one preferred embodiment for an impact collection surface 90 having a plurality of outwardly projecting rods 92 distributed thereon. The outwardly projecting rods increase the surface area of impact collection surface 90, which is provided with a coating 94 of one of the coating materials discussed above, and also increase the "roughness" of the surface to further enhance the collection efficiency of the coating. Coating 94 may be applied over rods 92 or applied before the rods are attached or formed on the impact collection surface. Alternative, other projecting structures such as ribs 96 may be employed on impact collection surface 90, as shown in FIG. 7B.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A method for separating particulates from a fluids in which said particulates are entrained, comprising the steps of:

(a) providing an impact collection surface;

(b) producing a coated impact collection surface by applying a coating of a material to the impact collection surface that increases a retention of particulates impacting thereon when the coated impact collect surface is dry, but releases the particulates when wetted, said coating comprising a material characterized by being hydrophilic in a first state and being hydrophobic in a second state, said material retaining the particulates when in the first state and releasing the particulates when in the second state; and (c) causing the fluid in which the particulates are entrained to flow toward the coated impact collection surface, said particulates within the fluid being retained by the material and thus separated from the fluid.

2. The method of claim 1, wherein the material employed to produce the coated impact collection surface is a bioselective coating that preferentially retains biological particulates impacting the coated impact collection surface.

3. The method of claim 2, wherein the bioselective coating comprises TETRAGLYME.

4. The method of claim 1, wherein the impact collection surface comprises a surface of a tape, and wherein the coating is applied to selected portions of the surface of the tape to produce the coated impact collection surface.

5. The method of claim 4, further comprising the step of advancing the tape, so that as the tape is advanced, new areas comprising the coated impact collection surface are impacted by particulates entrained in said fluid.

6. The method of claim 1, wherein the coated impact collection surface comprises a plurality of outwardly projecting structures that enhance collection of the particulates.

7. A method for separating particulates from a fluid in which said particulates are entrained, comprising the steps of:

(a) providing an impact collection surface;

(b) producing a coated impact collection surface by applying a coating of a material to the impact collection surface that increases a retention of particulates impacting thereon, wherein the material comprising the coating has a further property of attracting only particulates of a specific desired type; and (c) causing the fluid in which the particulates are entrained to flow toward the coated impact collection surface, said particulates within the fluid being retained by the material and thus separated from the fluid.

8. The method of claim 7, wherein the desired type of particulates are biological in nature.

9. The method of claim 8, wherein the coating comprises an antibody selected so that only particulates having a corresponding antigen are retained by the coating.

10. The method of claim 9, wherein the particulates retained by the coating comprise a disease causing organism.

11. The method of claim 7, wherein the fluid comprises a bodily fluid.

12. A method for separating particulates from a fluid in which said particulates are entrained, comprising the steps of:

(a) providing an impact collection surface;

(b) producing a coated impact collection surface by applying a coating of a material to the impact collection surface, the material comprising the coating being characterized by having a first state and a second state while coating the impact collection surface, said material retaining the particulates when in the first state, and releasing the particulates when in the second state; and (c) causing the fluid in which the particulates are entrained to flow toward the coated impact collection surface, said particulates within the fluid being retained by the material while said material is in the first state, and thus separated from the fluid.

13. The method of claim 12, further comprising the step of causing the material to change from the first state to the second state, in order to selectively release the particulates retained by the coating.

14. The method of claim 13, wherein the step of causing the material to change from the first state to the second state comprises the step of wetting the material with a liquid.

15. The method of claim 14, wherein the step of collecting comprises the steps of:

(a) directing the liquid toward the coated impact collection surface, so that the particulates that were separated from the fluid are carried away from the surface by the liquid after the material changes to the second state; and (b) collecting the liquid carrying the particulates.

16. The method of claim 14, wherein the liquid comprises water.

17. The method of claim 12, further comprising the steps of:

(a) causing the material to be in the second state after a defined period of time has elapsed with the material in the first state, during which the particulates are separated from the fluid and retained by the coating;

(b) causing the material comprising the coating to change from its first state to its second state; and (c) collecting the particulates that have been separated from the fluid, said particulates being released from the material when the material changes to its second state.

18. The method of claim 12, wherein the material comprises TETRAGLYME.

19. The method of claim 12, wherein the fluid is blood.

20. The method of claim 12, further comprising the step of collecting a specimen of the particulates retained on the coated impact collection surface.

21. The method of claim 20, wherein the step of collecting comprises the step of rinsing the particulates from the coated impact collection surface with a liquid stream that is directed at the coated impact collection surface.

22. Apparatus for separating particulates from a fluid in which they are entrained, comprising:

(a) an impact collection surface;

(b) a fluid path that conveys the fluid with the particulates toward the impact collection surface; and (c) a coating comprising a material that substantially enhances a retention and a collection of the particulates, by efficiently separating the particulates from said fluid, said material being characterized by being substantially non-tacky, and by readily releasing the particulates retained thereby when the material is wetted.

23. The apparatus of claim 22, wherein the material has a relatively low coefficient of friction, even when dry, such that any particles retained upon said coating are efficiently removed with a relatively small quantity of the liquid.

24. The apparatus of claim 23, wherein the material comprises PARYLENE.

25. The apparatus of claim 22, wherein the material comprising the coating is further characterized by attracting substantially only particulates of a specific desired type.

26. The apparatus of claim 25, wherein the coating comprises an antibody selected so that substantially only particulates having a corresponding antigen are retained by the coating.

27. The apparatus of claim 22, further comprising a fan to impel the fluid toward the impact collection surface, so that the particulates impact on the impact collection surface and are at least initially retained thereon.

28. The apparatus of claim 22, wherein the material releases the particulates when wetted with a liquid containing water.

29. Apparatus for separating particulates from a fluid in which they are entrained, comprising:

(a) an impact collection surface;

(b) a fluid path that conveys the fluid with the particulates toward the impact collection surface; and (c) a coating comprising a material that substantially enhances a retention and collection of the particulates, by efficiently separating the particulates from said fluid, said material being characterized by its ability to provide an increased retention of particulates impacting thereon when dry, and by having a relatively low coefficient of friction when wetted, so that the particulates that have impacted on the impact collection surface and been retained thereon are readily washed from said surface with a liquid, said material characterized by being hydrophilic when dry, and hydrophobic when wet.

30. The apparatus of claim 29, wherein the impact collection surface comprises a flexible, elongate strip.

31. The apparatus of claim 30, further comprising:

(a) a take-up reel for the flexible, elongate strip; and (b) a prime mover that is coupled to the take-up reel, said prime mover drivingly rotating the take-up reel to move the flexible, elongate strip past a point where the fluid path directs the fluid in which the particulates are entrained, to impact against said flexible, elongate strip.

32. The apparatus of claim 29, wherein the material comprises TETRAGLYME.

33. Apparatus for separating particulates comprising biological matter from a fluid in which they are entrained, comprising:

(a) an impact collection surface;

(b) a fluid path that conveys the fluid with the particulates toward the impact collection surface; and (c) a coating comprising a material that attracts substantially only biologic particulates of a specific desired type, for efficiently separating said particulates from said fluid, said coating binding with the particulates of the specific desired type to retain them on the impact collection surface.

34. The apparatus of claim 33, wherein the coating comprises an antibody that binds with an antigen on the biological matter.

35. Apparatus for separating particulates from a fluid in which they are entrained, comprising:

(a) an impact collection surface;

(b) a fluid path that conveys the fluid with the particulates toward the impact collection surface; and (c) a coating disposed on the impact collection surface and comprising a material that changes state while being retained on the impact collection surface, a first state of the material being characterized by its ability to retain the particulates that impact thereon, separating the particulates from the fluid, and a second state of the material being characterized by its ability to readily release the particulates separated from the fluid.

36. The apparatus of claim 35, wherein the impact collection surface comprises a plurality of outwardly projecting structures that enhance collection of the particulates.

37. The apparatus of claim 35, wherein the material comprises TETRAGLYME.

38. A method for separating particulates from a fluid in which said particulates are entrained, comprising the steps of:

(a) providing an impact collection surface;

(b) producing a coated impact collection surface by applying a coating of a material to the impact collection surface that enhances a retention and a collection of the particulates, by efficiently separating the particulates from said fluid, said material being substantially non-tacky, so that the particulates that have impacted on the impact collection surface and been retained thereon are readily washed from said surface with a liquid, said material further being characterized by attracting substantially only particulates of a specific desired type; and (c) causing the fluid in which the particulates are entrained to flow toward the coated impact collection surface, said particulates within the fluid being retained by the material and thus separated from the fluid.

39. The method of claim 38, wherein the coating comprises an antibody selected so that substantially only particulates having a corresponding antigen are retained by the coating.

40. A method for separating particulates from a fluid in which said particulates are entrained, comprising the steps of:

(a) providing an impact collection surface;

(b) producing a coated impact collection surface by applying a coating of a material to the impact collection surface that enhances a retention and a collection of the particulates, by efficiently separating the particulates from said fluid, said material being substantially non-tacky and having a relatively low coefficient of friction, even when dry, such that the particulates that have impacted on the impact collection surface and have been retained thereon are readily and efficiently washed from said surface with a liquid, said coating comprising PARYLENE; and (c) causing the fluid in which the particulates are entrained to flow toward the coated impact collection surface, said particulates within the fluid being retained by the material and thus separated from the fluid.

* * * * *